(12) United States Patent
Roehrig et al.

(10) Patent No.: US 6,640,001 B2
(45) Date of Patent: *Oct. 28, 2003

(54) METHOD AND APPARATUS FOR FAST DETECTION OF LESIONS

(75) Inventors: Jimmy R. Roehrig, Palo Alto, CA (US); Harlan M. Romsdahl, Half Moon Bay, CA (US); Wei Zhang, Mountain View, CA (US)

(73) Assignee: R2 Technology, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/907,585

(22) Filed: Jul. 17, 2001

(65) Prior Publication Data

US 2002/0003894 A1 Jan. 10, 2002

Related U.S. Application Data

(63) Continuation of application No. 09/103,290, filed on Jun. 23, 1998, now Pat. No. 6,263,092, which is a continuation of application No. 08/676,660, filed on Jul. 10, 1996, now Pat. No. 5,815,591.

(51) Int. Cl.⁷ ................................................ G06K 9/00
(52) U.S. Cl. ........................................ 382/128; 382/194
(58) Field of Search ........................ 382/100, 128–134, 382/155, 172, 181; 600/300, 410, 428, 407; 128/915, 653; 378/155, 21, 37; 250/236, 584

(56) References Cited

U.S. PATENT DOCUMENTS

| 4,839,807 | A | * | 6/1989 | Doi et al. | 382/128 |
| 4,856,528 | A | * | 8/1989 | Yang et al. | 128/653 |
| 5,003,979 | A | * | 4/1991 | Merickel et al. | 128/653 |
| 5,123,054 | A | * | 6/1992 | Hara et al. | 382/128 |
| 5,212,637 | A | * | 5/1993 | Saxena | 600/407 |
| 5,231,580 | A |   | 7/1993 | Cheung et al. | 382/128 |
| 5,343,390 | A | * | 8/1994 | Doi et al. | 382/128 |
| 5,768,406 | A | * | 6/1998 | Abdel-Mottaleb | 382/132 |
| 5,799,100 | A | * | 8/1998 | Clarke et al. | 382/132 |
| 5,889,881 | A |   | 3/1999 | MacAulay et al. | 382/133 |
| 5,937,083 | A |   | 8/1999 | Ostuni | 382/131 |

* cited by examiner

Primary Examiner—Jayanti K. Patel
(74) Attorney, Agent, or Firm—Pennie & Edmonds LLP

(57) ABSTRACT

A method and apparatus for the fast detection of spiculated lesions in a digital mammogram, the method for use in a computer aided diagnosis system for assisting a radiologist in identifying and recognizing the spiculations among a multiplicity of lines corresponding to standard fibrous breast tissue. A line and direction image is created from a digital mammogram, and a region of potential intersection for substantially every pixel in the digital mammogram image is determined. The region of potential intersection for each pixel is a predetermined pattern, such as a high aspect ratio rectangle or trapezoid, positioned around the pixel and rotated in a direction corresponding to direction information for that pixel. The regions of potential intersection are accumulated among the pixels to produce a cumulative array, and information in the cumulative array is processed for identifying spiculations in the digital mammogram.

24 Claims, 9 Drawing Sheets

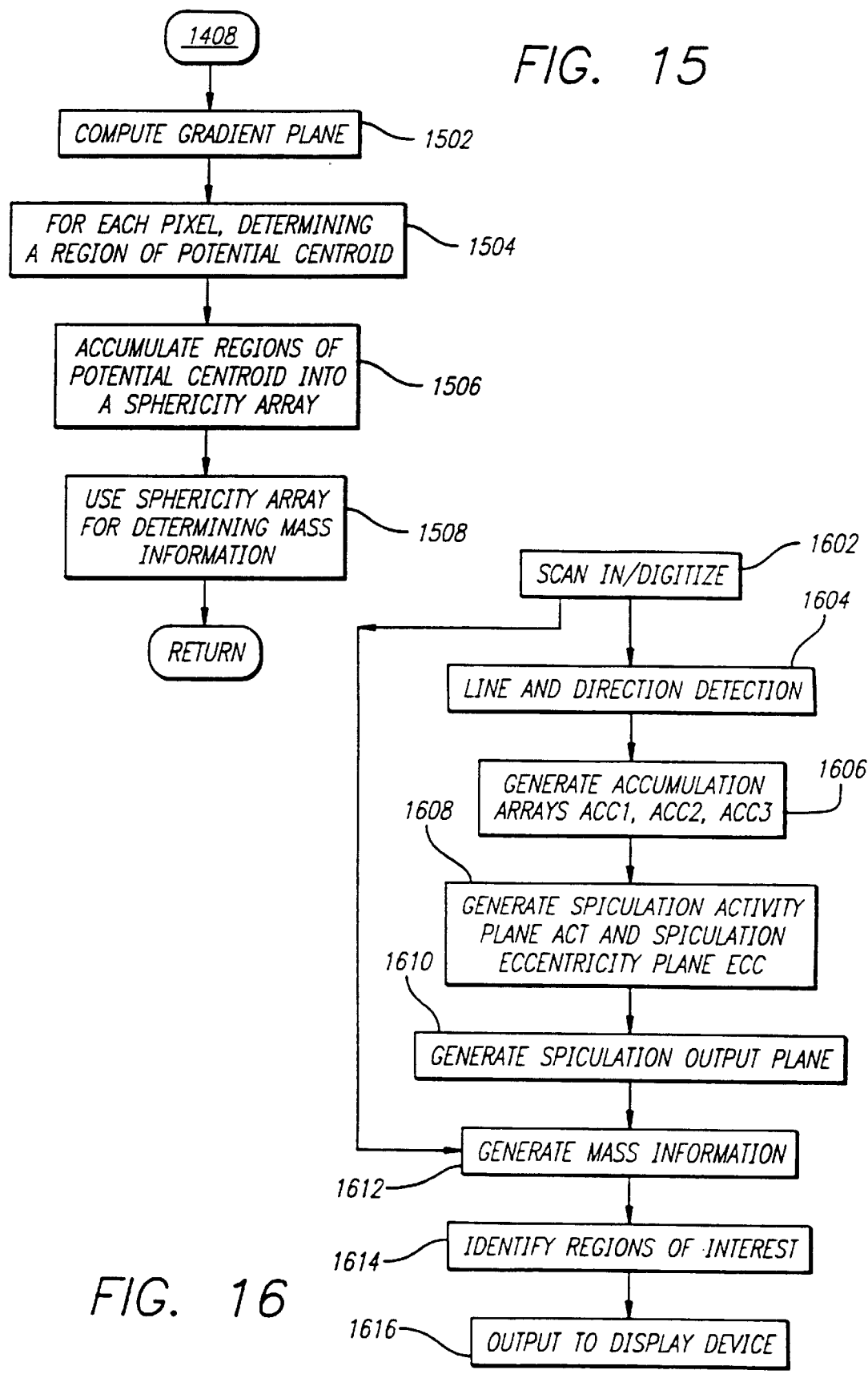

METHOD AND APPARATUS FOR FAST DETECTION OF LESIONS

This application is a continuation of prior U.S. application Ser. No. 09/103,290, filed Jun. 23, 1998, now U.S. Pat. No. 6,263,092 which is a continuation of Ser. No. 08/676,660 filed Jul. 10, 1996 now U.S. Pat. No. 5,815,591.

FIELD OF THE INVENTION

The present invention relates to the field of computer aided diagnosis of abnormal lesions in medical images. In particular, the invention relates to a fast algorithm for detecting spiculated or stellar lesions in a digital mammogram to assist in the detection of malignant breast cancer tumors at an early stage in their development.

BACKGROUND OF THE INVENTION

Breast cancer in women is a serious health problem, the American Cancer Society currently estimating that over 180,000 U.S. women are diagnosed with breast cancer each year. Breast cancer is the second major cause of cancer death among women, the American Cancer Society also estimating that breast cancer causes the death of over 44,000 U.S. women each year. While at present there is no means for preventing breast cancer, early detection of the disease prolongs life expectancy and decreases the likelihood of the need for a total mastectomy. Mammography using x-rays is currently the most common method of detecting and analyzing breast lesions.

The detection of spiculated, or stellar-shaped, lesions ("spiculations") in mammograms is of particular importance because a spiculated breast tumor has a relatively high probability of being malignant. While it is important to detect the spiculated lesions as early as possible, i.e. when they are as small as possible, practical considerations can make this difficult. In particular, a typical mammogram may contain myriads of lines corresponding to fibrous breast tissue, and the trained, focused eye of a radiologist is needed to detect small spiculated lesions among these lines. Moreover, a typical radiologist may be required to examine hundreds of mammograms per day, leading to the possibility of a missed diagnosis due to human error.

Accordingly, the need has arisen for a computer-assisted diagnosis (CAD) system for assisting in the detection of abnormal lesions, including spiculations, in medical images. The desired CAD system digitizes x-ray mammograms to produce a digital mammogram, and performs numerical image processing algorithms on the digital mammogram. The output of the CAD system is a highlighted display which directs the attention of the radiologist to suspicious portions of the x-ray mammogram. The desired characteristics of a spiculation-detecting CAD system are high speed (requiring less processing time), high precision (the ability to detect subtle spiculations), and high accuracy (the ability to avoid false positives and missed spiculations). It may also be desired that the spiculation-detecting CAD system also be used as a mass-detecting and mass-classifying CAD system, and that the CAD system be capable of using spiculation information in conjunction with mass information for identifying suspicious masses in the digital mammogram and directing the attention of the radiologist to both the spiculations and the suspicious masses.

One method for detecting spiculations in digital mammograms, proposed by Kegelmeyer et al and referred to as the "Alignment of Local Oriented Edges" (ALOE) algorithm, is described in Kegelmeyer, "Computer-aided Mammographic Screening for Spiculated Lesions," Radiology 191:331–337 (1994). The ALOE method first calculates local gradients in a digitized mammogram. For each "candidate point" in the image, a predetermined window around that point is selected, the window size being some fraction of the overall image size. An "ALOE signal" for each candidate point then is calculated based on information in the surrounding window, the ALOE signal being defined as the standard deviation of a histogram of the gradient directions of all pixels in the window. The next candidate point, offset from the previous candidate point by a distance corresponding to the desired resolution of the search, is then considered.

Keeping in mind that a spiculation is a roughly symmetric set of lines radiating from a central point or region, a histogram of gradient directions will tend to be a flat distribution from 0 to 360 degrees if a spiculated region is centered around the candidate point. Thus, because the ALOE signal is the standard deviation of the histogram, the ALOE signal will be lower for those candidate points which are at the centers of spiculations, and will be higher for those candidate points which are not at the centers of spiculations. After the ALOE signal is calculated for all candidate points in the image, local minima in a plot of the ALOE signals are used as a basis for identifying spiculations.

The ALOE algorithm has several disadvantages. The primary disadvantage is that, in addition to spiculations, many unwanted background objects can also produce a small ALOE signal. For example, a point that is surrounded by a circle, such as the border of a circumscribed mass, also produces gradients in all directions, and therefore will produce a local minimum ALOE signal. A false positive may result. Furthermore, a typical spiculation in an actual mammogram will not have lines radiating in every direction, but rather will have lines radiating in several discrete directions in rough symmetry about the center. Thus, because every direction may not be present in the histogram of gradient angles around the center of a spiculation, the standard deviation of the histogram may still be quite large, resulting in a larger ALOE signal. This spiculation may then be missed. Thus, the ALOE algorithm represents serious practical problems because it may yield false positives and may also miss certain spiculations.

The ALOE algorithm is representative of a class of "backward direction" spiculation detection algorithms. By "backward direction" it is meant that a "candidate point" is incrementally moved across the image by a distance corresponding to the desired resolution of the spiculation search. At each candidate point, a set of "window computations" for a window of pixels surrounding the candidate point is performed, and a metric corresponding to the presence and/or strength of a spiculation centered on the candidate point is computed. Thus, for example, the ALOE algorithm computes the "ALOE signal" for each candidate point, and then moves on to the next candidate point.

As a general observation, "backward direction" algorithms are computationally intensive. This is because, for an image size of N×N, there will generally need to be on the order of $K(bN)^2$ computations, where K is the number of window computations for each candidate point, and where b is the reciprocal of the number of image pixels between each candidate point. Because the number K is often proportional to the square or cube of the window size, the computational intensity of "backward direction" approaches can easily get out of hand.

A second method for detecting spiculations in digital mammograms, proposed by Karssemeijer et al., is described in Karssemeijer, "Recognition of Stellate Lesions in Digital Mammograms," *Digital Mammography: Proceedings of the 2nd International Workshop on Digital Mammography, York, England, Jul.* 10–12 1994 (Elsevier Science 1994), and "Detection of Stellate Distortions in Mammograms using Scale Space Operators," *Information Processing in Medical Imaging* (Bizais et al., eds., Kluwer Academic Publishers 1995). Like the ALOE algorithm, the Karssemeijer approach is also a "backward direction" spiculation detection algorithm.

In the Karssemeijer algorithm, a "line image" and a "direction image" is first formed from the digital mammogram. As is known in the art, a line image contains line information for each pixel in the digital mammogram, while a direction image contains direction information for each pixel in the line image. The most basic form of line image, used in the Karssemeijer algorithm, contains line information which is a "1" if the pixel is located along a line and a "0" otherwise. The most basic form of direction image, also used in the Karssemeijer algorithm, contains direction information which, for those pixels having a "1" in the line image, equals the approximate angle of a tangent to the line passing through the pixel.

Consistent with its "backward direction" character, the Karssemeijer algorithm then considers a window of pixels, chosen to be an annulus, around a candidate point in the line image, and then computes a metric associated with that candidate point. This procedure is repeated for each candidate point. The metric for each candidate point is calculated by counting the number of pixels in the annular window which are contained along lines which point approximately to the center of the window. Local maxima in a plot of the metrics are used to identify spiculations in the image.

The Karssemeijer algorithm has several disadvantages. The primary disadvantage is computational intensity due to the "backward direction" character of the algorithm. Because each line image pixel actually appears in many sequential windows corresponding to successive candidate points, the calculations are repeated for each pixel many times, and the algorithm is very time consuming. As discussed previously, speed is a key factor in a CAD system for assisting a radiologist. A CAD device which slows down the radiologist, who must often view and analyze hundreds of mammograms per day, is undesirable.

Further, the approach used by Karssemeijer in the detection of lines for generating the line image is based on using Gabor filters in the frequency domain and performing a Fast Fourier Transform (FFT) on the mammogram image. The image pixels are then multiplied by the transformed Gabor kernel elements, and the inverse FFT is then used to obtain the enhanced line image in the spatial domain. This approach requires input images which have dimensions that are a power of two, which is required by the FFT. Thus, after digitizing the mammogram, the Karssemeijer approach requires the digitized image to be "padded out" to the nearest power of two. The cost of this approach is higher memory requirements in the computer and a larger computation time.

Accordingly, it is an object of the present invention to provide a fast computer-assisted diagnosis (CAD) system for assisting in the identification of spiculated lesions in digital mammograms, the CAD system being capable of producing an output which directs attention to spiculated lesions in the x-ray mammogram for increasing the speed and accuracy of x-ray mammogram analysis.

It is a further object of the present invention to provide a fast CAD system for detecting spiculated lesions which produces fewer false positives and fewer missed spiculations, while also being capable of detecting smaller spiculations.

It is still a further object of the present invention to provide a fast CAD system which detects spiculated lesions in a manner fast enough to permit use of the CAD system in a clinical radiology environment.

It is still a further object of the present invention to provide a fast spiculation-detecting CAD system which is also capable of detecting and classifying masses in a digital mammogram, the CAD system being capable of using spiculation information in conjunction with mass information for identifying suspicious masses in the digital mammogram.

SUMMARY OF THE INVENTION

These and other objects of the present invention are provided for by an improved CAD system for detecting spiculated lesions in a digital mammogram image using a "forward direction" detection algorithm, as opposed to a "backward direction" detection algorithm, for improving the speed, accuracy, and precision of results. A CAD system according to the present invention employs a fast method for detecting spiculations in the digital mammogram image, the method including the steps of determining a region of potential intersection for a plurality of pixels using line information and direction information related to the pixel, accumulating the regions of potential intersection to produce a cumulative array, and using information derived from the cumulative array, such as the positions and strengths of local maxima in the cumulative array, for identifying the spiculations in the digital mammogram image. In one embodiment of the invention, the region of potential intersection for every pixel in the digital mammogram image is determined and accumulated into the cumulative array.

The line information and direction information are obtained by generating a line image and a direction image corresponding to the digital mammogram image. The region of potential intersection corresponding to a pixel is found by determining, according to the line information related to the pixel, whether the pixel is located along a line, and if the pixel is located along a line, selecting a region centered on the pixel corresponding to a predetermined pattern, the predetermined pattern being rotated by an amount related to the direction information related to the pixel. In another embodiment of the invention, the amount by which the predetermined pattern is rotated is equal to the direction information for that pixel. In another embodiment of the invention, the predetermined pattern is a split rectangle or trapezoid centered on the pixel, the rectangle or trapezoid having a large aspect ratio. The spiculations are identified by using information from the cumulative array formed by an accumulation of the regions of potential intersection for the pixels in the image.

Advantageously, a given pixel in the digital mammogram image is considered only once in the process of developing the cumulative array. In this sense, a CAD system according to the present invention operates in the "forward direction," and is very fast when compared to the "backward direction" algorithms presented previously, which use image pixels multiple times in deriving spiculation metrics. Thus, the method used in a CAD system according to the present invention is very fast. Moreover, the method is highly amenable to hardware implementation using parallel processors, thus increasing the speed of the CAD system even further.

In another embodiment of the present invention, the cumulative array comprises fewer pixels than the digital mammogram image. For example, where the digital mammogram image is M×N pixels, the cumulative array may be 0.25M×0.25N pixels. Using line information and direction information related to each digital mammogram pixel, a region of potential intersection is determined for each pixel with respect to the smaller cumulative array and proportionally located in a smaller 0.25M×0.25N space. The regions of potential intersection are then accumulated into the 0.25M× 0.25N cumulative array. Because there are addition operations taking place for fewer cumulative array pixels, the algorithm is made significantly faster without a significant loss in resolution.

In another embodiment of the invention, the CAD system performs the step of computing line information and direction information for each image pixel in the digital mammogram, followed by the step of computing a weighting function WT(theta) based on statistical information taken among direction information for all image pixels. The direction information for each digital mammogram image pixel having coordinates (i,j) is an angle THETA(i,j), and the weighting function WT(theta) is equal to WT(THETA(i,j)) for that pixel. For each digital mammogram pixel, a region of potential intersection is determined and accumulated into the cumulative array after being weighted by WT(THETA (i,j)) for that pixel. The weighting function WT(theta) is computed by calculating a histogram function H(theta) of the direction information THETA(i,j) for all image pixels, followed by the step of developing the function WT(theta) as having an inverse relationship to the histogram function H(theta). In this manner, lines perpendicular to a predominant line direction in the digital mammogram image are emphasized, whereas lines parallel to the predominant line direction in the digital mammogram are de-emphasized, thus increasing system precision and accuracy.

In another embodiment of the present invention, mass information corresponding to the digital mammogram image, including mass location information, is computed in addition to the cumulative array. Information in the cumulative array is used in conjunction with the mass information for identifying regions of interest in the digital mammogram image, such as by using a linear classifier method based on mass information and cumulative array metrics.

In another embodiment of the invention, local attention is given to the cumulative array near locations having a strong circumscribed mass candidate. The cumulative array is thresholded by a first threshold value in a first region not including the strong circumscribed mass candidate location, whereas the cumulative array is thresholded by a second value less than the first value in a second region which includes said strong circumscribed mass candidate. In this manner, spiculations which otherwise would have fallen below a threshold value in the cumulative array are detected when associated with a strong circumscribed mass candidate, for assigning a value of spiculatedness to said circumscribed mass candidate in mass detection and classification.

In another embodiment of the invention, mass information for the digital mammogram image is computed by using information in a sphericity array. The sphericity array is calculated by the steps of computing a gradient plane from the digital mammogram image, the gradient plane having pixels, each gradient plane pixel having a gradient intensity value and a gradient direction value, determining a region of potential centroid for each gradient plane pixel using the gradient intensity value and gradient direction value for that pixel, and accumulating the regions of potential centroid to produce a sphericity array. In this way, strong circumscribed mass candidates may be detected by using information derived from an algorithm which is a forward direction algorithm similar to the forward direction algorithm for detecting spiculations.

In another embodiment of the present invention, the fast CAD system is capable of locating noneccentric spiculations for increased precision, accuracy, and reduction of false positives. The fast CAD system according to this embodiment performs a method comprising the steps of determining a region of potential intersection for each of a plurality of image pixels using line information and direction information related to that image pixel, computing a plurality of weights corresponding to each of the plurality of image pixels, accumulating for each of the plurality of image pixels a plurality of weights into a plurality of accumulation planes for those pixels located within the region of potential intersection for that image pixel, and processing information contained in said plurality of accumulation planes for identifying the noneccentric spiculations in the image. The plurality of accumulation planes comprises a first accumulation plane ACC1, a second accumulation plane ACC2, and a third accumulation plane ACC3, the first, second, and third accumulation planes ACC1, ACC2, and ACC3 being processed for producing a spiculation activity plane ACT and a spiculation eccentricity plane ECC for use in locating noneccentric spiculations.

The spiculation activity plane ACT and the spiculation eccentricity plane ECC are computed using information in the plurality of accumulation planes such that the spiculation activity plane ACT comprises pixel values related to the presence of spiculations, and such that said spiculation eccentricity plane ECC comprises pixel values related to the presence of eccentric spiculations. A spiculation output plane SO is formed by setting, for each pixel (i,j), SO(i,j) equal to a first constant multiplied by ACT(i,j) added to a second constant multiplied by ECC(i,j), the first constant typically being a positive number and the second constant usually being about −0.5 times the first constant. In this manner, the spiculation output plane SO(i,j) will contain high values near locations having spiculations, and will contain maxima among these high values corresponding to spiculations which are less eccentric and more radially symmetric. In this manner, false positives are reduced and accuracy and precision are increased.

In another embodiment of the invention, mass information corresponding to the digital mammogram image is computed, the mass information including mass events, each event comprising mass centroid location, mass area, mass elongation, and mass contrast. Information contained in the SO, ACT, and ECC arrays is used in conjunction with the mass information in a linear classifier method for identifying regions of interest in the image.

BRIEF DESCRIPTION OF THE DRAWINGS

FIG. 15 shows a flowchart representing a sphericity algorithm in accordance with a further embodiment of the present invention;

FIG. 16 shows a flowchart representing a spiculation detection algorithm using multiple accumulation planes in accordance with a preferred embodiment of the present invention.

DETAILED DESCRIPTION OF THE INVENTION

Figure 1A:
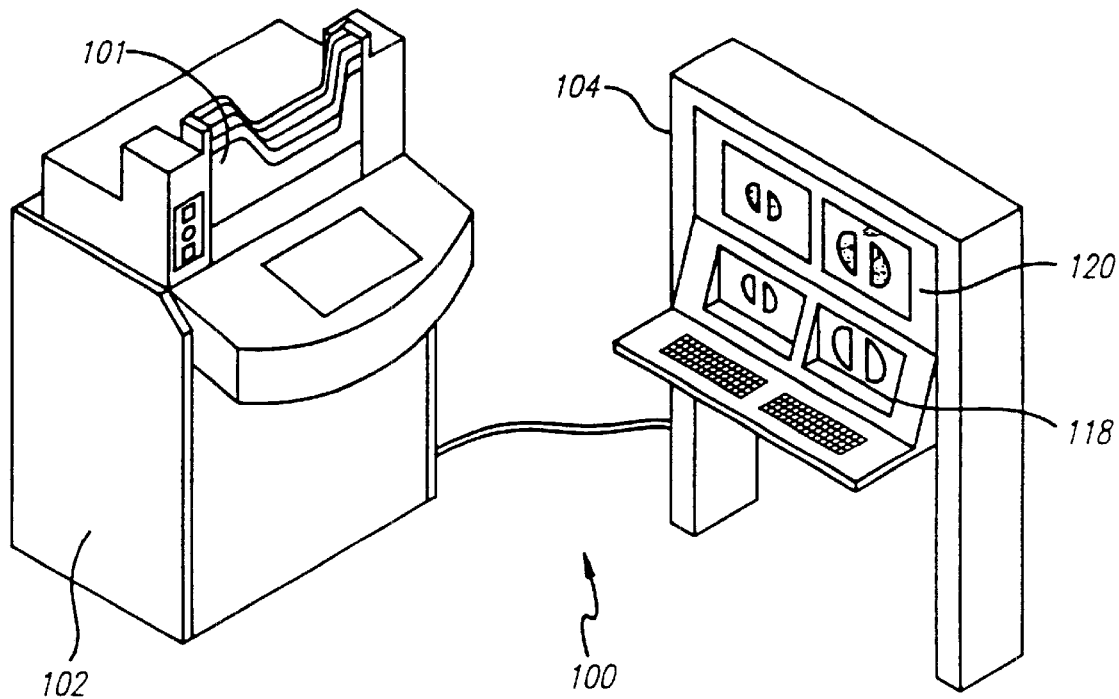
FIG. 1a shows an outside view of a computer aided diagnostic (CAD) system according to the present invention.

FIG. 1a shows an outside view of a computer aided diagnostic (CAD) system 100 for assisting in the identification of spiculated lesions in mammograms according to the present invention. CAD system 100 is used as a step in the processing of films for mammography exams. CAD system 100 comprises a CAD processing unit 102 and a viewing station 104. In general, CAD processing unit 102 scans an x-ray mammogram into a digital mammogram image, processes the image, and outputs a highlighted digital mammogram for viewing at viewing station 104.

Figure 1B:
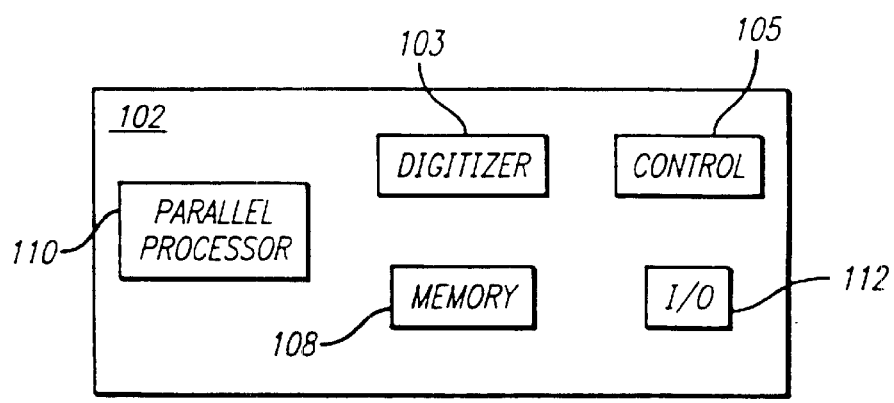
FIG. 1b shows a block diagram of a CAD processing unit of a CAD system according to the present invention.

FIG. 1b shows a block diagram of CAD processing unit 102. CAD processing unit 102 comprises a digitizer 103, such as a laser scanner with 50 micron resolution, for digitizing a developed x-ray mammogram 101, the x-ray mammogram 101 being shown in FIG. 1a at an input to the CAD processing unit 102. CAD processing unit 102 generally includes elements necessary for performing image processing including parallel processing steps. In particular, CAD processing unit 102 includes elements such as a central control unit 105, a memory 108, a parallel processing unit 110, and I/O unit 112. It is to be appreciated that in addition to the spiculation detection algorithms disclosed herein, processing unit 102 is capable of performing a multiplicity of other image processing algorithms such as mass detection and linear classification algorithms, either serially or in parallel with the disclosed spiculation detection algorithms.

Viewing station 104 is for conveniently viewing both the x-ray mammogram 101 and the output of the CAD processing unit 102 on a display device 118. The display device 118 may be, for example, a CRT screen. The display device 118 typically shows a highlighted digital mammogram corresponding to the x-ray mammogram 101, the highlighted digital mammogram having information directing the attention of the radiologist to special areas which may contain spiculations as determined by image processing steps performed by the CAD processing unit 102. In one embodiment of the invention, the highlighted digital mammogram will have black or red circles superimposed around those locations corresponding to spiculated lesions.

Viewing station 104 also comprises a backlighting station 120 for viewing the actual x-ray mammogram 101 itself. The radiologist is assisted by the CAD system 100 by viewing the display device 118, which then directs the attention of the radiologist to the spiculated portions of the actual x-ray mammogram 101 itself. It is to be appreciated that the CAD processing unit 102 is capable of performing other image processing algorithms on the digital mammogram in addition to or in parallel with the algorithm for detecting spiculations in accordance with the present invention. In this manner, the radiologist may be informed of several suspicious areas of the mammogram at once by viewing the display device 118, spiculations being one special type of the suspicious area.

After x-ray mammogram 101 has been developed, it is inserted into the CAD system 100, which will ideally be located near the x-ray development area of a mammography clinic. After being digitized by digitizer 103, the x-ray mammogram will be transported using means not shown to the viewing station 104 for viewing by the radiologist along with the output of the display device 118 as described above. After the x-ray mammogram 101 has passed through the CAD system 100, it will be taken away and will undergo the same processing currently practiced in clinics. It is to be noted that memory 108 of CAD processing unit 102 may be used in conjunction with I/O unit 112 to generate a permanent record of the highlighted digital mammogram described above, and/or may also be used to allow non-real-time viewing of the highlighted digital mammogram.

Figure 2:
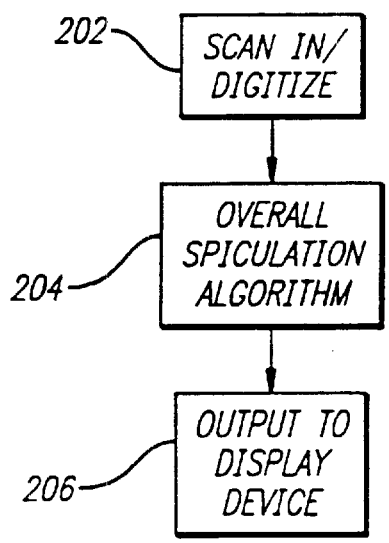
FIG. 2 is a flowchart representing overall steps practiced by the system of FIG. 1.

FIG. 2 shows the general steps performed by CAD processing unit 102 on the x-ray mammogram. At step 202, the x-ray mammogram is scanned in and digitized into a digital mammogram. The digital mammogram may be, for example, a 3000×4000 array of 12-bit gray scale pixel values. Such a digital mammogram would generally correspond to a typical 8"×10" x-ray mammogram which has been digitized at a 50 micron spatial resolution. Because a full resolution image such as the 3000×4000 image described above is not necessary for the effectiveness of the present invention, the image may be locally averaged, using steps known in the art, down to a smaller size corresponding, for example, to a 200 micron spatial resolution. At such a resolution, a typical image would then be an M×N array of 12-bit gray scale pixel values, with M being near 900, for example, and N being near 1200, for example. In general, however, either the full resolution image or the locally averaged image may be used as the original digital mammogram in accordance with the present invention. Without limiting the scope of the present invention, and for clarity of disclosure, the "digital mammogram image" is considered to be an exemplary M×N array of 12-bit gray scale pixel values.

FIG. 2 shows the digital mammogram image being processed at step 204 by an overall spiculation algorithm in accordance with the present invention. As discussed previously, the overall spiculation algorithm performed at step 204 generates a list of locations in the digital mammogram image which may correspond to spiculations, along with information such as spiculation intensity for each location. Following step 204, the digital mammogram image and list of spiculation locations and information is sent for display to the viewing station 104 at step 206.

Figure 3:
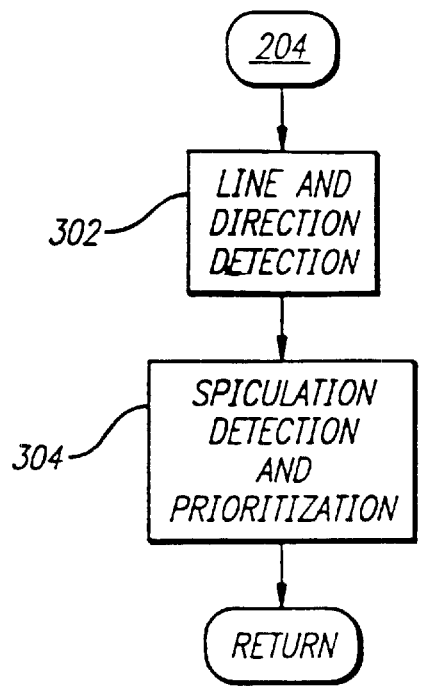
FIG. 3 is a flowchart representing overall steps taken in the spiculation detection algorithm portion of FIG. 2.

FIG. 3 shows in more detail the steps associated with the overall spiculation algorithm of step 204 of FIG. 2. In particular, the overall spiculation algorithm comprises the step of generating an M×N line image and an M×N direction image from the digital mammogram image at line and direction detection step 302. The M×N line image generated at step 302 comprises, for each pixel (i,j), line information in the form of a "1" if the pixel (i,j) has a line passing through it, and a "0" otherwise. The M×N direction image further comprises, for each pixel (i,j), direction information in the form of a number THETA. If the line information is a "1" for the line image pixel (i1,j1), the number THETA for the pixel (i1,j1) corresponds to an estimated direction of the tangent to the line passing through (i1, j1).

FIG. 3 also shows a spiculation detection and prioritization step 304 following line and direction detection step 302. Spiculation detection and prioritization step 304 comprises the step of identifying, classifying, and prioritizing spiculations in the digital mammogram image by processing information in the line image and direction image generated by line and direction detection step 302.

Figure 4:
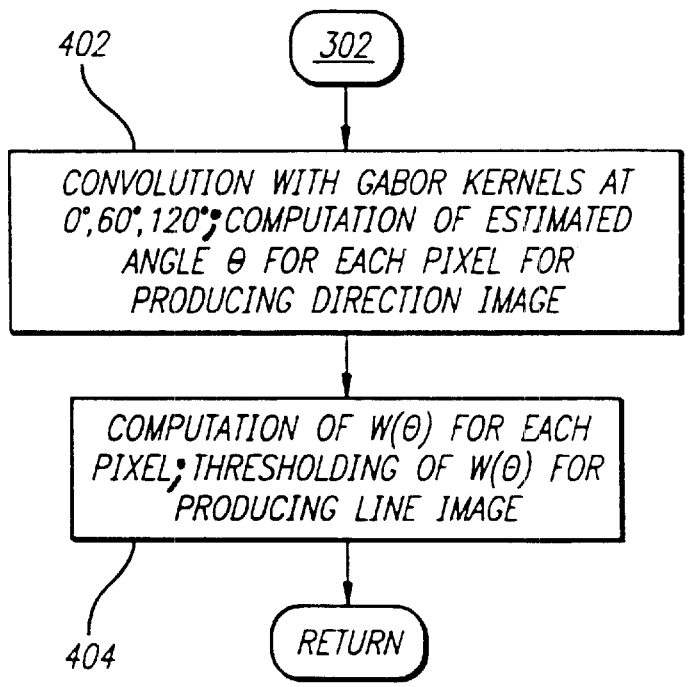
FIG. 4 is a flowchart representing line detection and direction estimation steps for producing a line image and a direction in accordance with the present invention.

FIG. 4 shows steps corresponding to the line and direction detection step 302 of FIG. 3. Shown at FIG. 4 is the direction detection step 402 for detecting at each pixel (i,j) a direction corresponding to a lines, if any, passing through the pixel (i,j) in the digital mammogram image. Direction detection step 402 comprises the step of separately convolving the digital mammogram image with three Gabor kernels K(0), K(60), and K(120). The Gabor kernels are derived from the Gabor filter which, as known in the art, is the second derivative of a Gaussian kernel given by:

$$G(r, \sigma) = \frac{1}{2\pi\sigma^2} \exp((-r^2)/(2\sigma^2)) \quad (1)$$

The second derivative of this function with respect to x, quantized into a finite sized integer array, yields the K(0) kernel. Further, by rotating this array by 60 degrees and 120 degrees, the two other kernels K(60) and K(120) are obtained. The step of separately convolving the digital mammogram with the kernels K(0), K(60), and K(120) yields three images W(0), W(60), and W(120), respectively.

At step 402, direction information theta(i,j) for each pixel (i,j) is obtained by using a formula such as that disclosed in Koenderink and Van Doorn, "Generic Neighborhood Operators," *IEEE Transactions on Pattern Analysis and Machine Intelligence,* Vol. 14, No. 6 (June 1992) and given by:

$$\theta = \frac{1}{2} a\tan\sqrt{3}\left(\frac{W(60) - W(120)}{W(60) + W(120) - 2W(0)}\right) \quad (2)$$

FIG. 4 further shows line detection step 404 for detecting line information in the digital mammogram image. Positive contrast (light) lines are important, as opposed to negative contrast (dark) lines, since the former is how spiculations are manifested in x-ray films. Line detection step 404 comprises the step of deriving a function W(THETA) from the images W(0), W(60), and W(120) using a formula disclosed in the Koenderink reference cited supra:

$$W_\sigma(\theta) = \frac{1}{3}(1 + 2\cos(2\theta))W_\sigma(0) + \frac{1}{3}(1 - \cos(2\theta) + \sqrt{3}\sin(2\theta)) \quad (3)$$

$$W_\sigma(60) + \frac{1}{3}(1 - \cos(2\theta) - \sqrt{3}\sin(2\theta))W_\sigma(120)$$

After being computed, W(THETA) is thresholded at some positive value for obtaining a binary line image.

Figure 5:
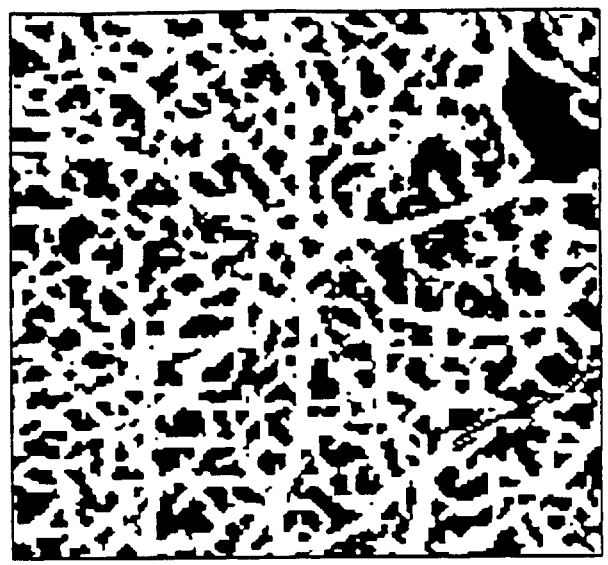
FIG. 5 shows a portion of a binary line image corresponding to a digital mammogram image

FIG. 5 shows a portion of binary line image corresponding to a digital mammogram image, the white pixels corresponding to a value "1" and the dark pixels corresponding to a value of "0". The significance of the binary line image is that every point in the white (line) areas of the binary line image belongs to a line of sufficient strength to exceed the threshold chosen.

Thus, after step 404 of FIG. 4, there exists a line image and a direction image corresponding to the digital mammogram image available for further processing by the spiculation detection and prioritization step 304 of FIG. 3. While there are several methods known in the art for line and direction detection, the above approach is employed in a preferred embodiment of the present invention because the computationally intensive parts consist of the three convolutions performed to obtain W(0), W(60), and W(120), and these convolutions are easily implemented in a highly parallel processor such as that used in processing unit 104. By implementing these convolutions in the spatial domain in a hardware parallel processor, the speed of computation easily meets normal through-put requirements for clinical practice. For notational simplicity, the direction information in the direction image corresponding to a pixel (i,j) will be denoted THETA(i,j).

Figure 6:
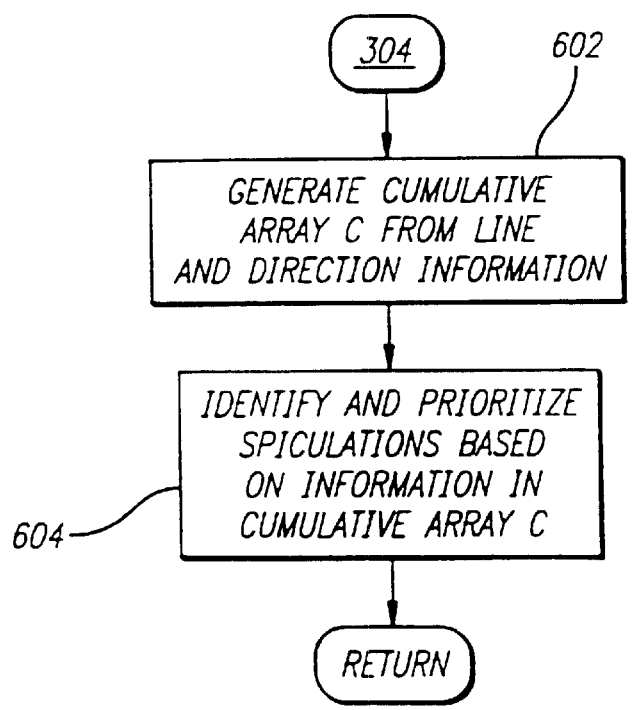
FIG. 6 is a flowchart representing a spiculation detection algorithm in accordance with one embodiment of the present invention.

FIG. 6 shows a block diagram outlining steps for accomplishing the spiculation detection and prioritization step 304 of FIG. 3. In particular, FIG. 6 shows the feed-forward step 602 of generating a cumulative array C from line and direction information corresponding to each pixel in the line image. The cumulative array C, which is generally the same size as the M×N digital mammogram image, the M×N line image, and the M×N direction image, is first initialized. Then each pixel (i,j) in the digital mammogram image is considered. In particular, if a pixel (i,j) has line image information with a value "0", it is ignored. However, if the pixel (i,j) has line image information with a value "1", the cumulative array C is incremented by a constant value for each pixel located in a region corresponding to a predetermined pattern centered at the pixel location (i,j). The predetermined pattern is generally a split rectangular or trapezoidal pattern of pixels having a high aspect ratio, rotated at an angle corresponding to the direction information for the pixel (i,j). The next pixel in the digital mammogram image is then considered. After each pixel in the digital mammogram image is considered, the cumulative array C will be completely formed.

FIG. 6 further shows a step 604 for identifying and prioritizing spiculations based on information contained in the cumulative array C. Generally, the cumulative array C will contain values C(i,j) corresponding to the strength of spiculations centered on the digital mammogram pixel located at coordinates (i,j). Generally, the cumulative array C will contain local maxima where spiculations, if any, are likely to be present. The cumulative array C may be processed in a variety of ways for identifying locations and strengths of spiculations in the digital mammogram image.

For example, in the simplest procedure, step 604 may comprise the step of identifying those locations (i,j) in the cumulative array C for which C(i,j) is greater than a predetermined threshold value. However, other ways for identifying and prioritizing spiculations based on information contained in the cumulative array C, many of which will be apparent to one of ordinary skill in the art upon reading this disclosure, may be used in step 604.

Figure 7:
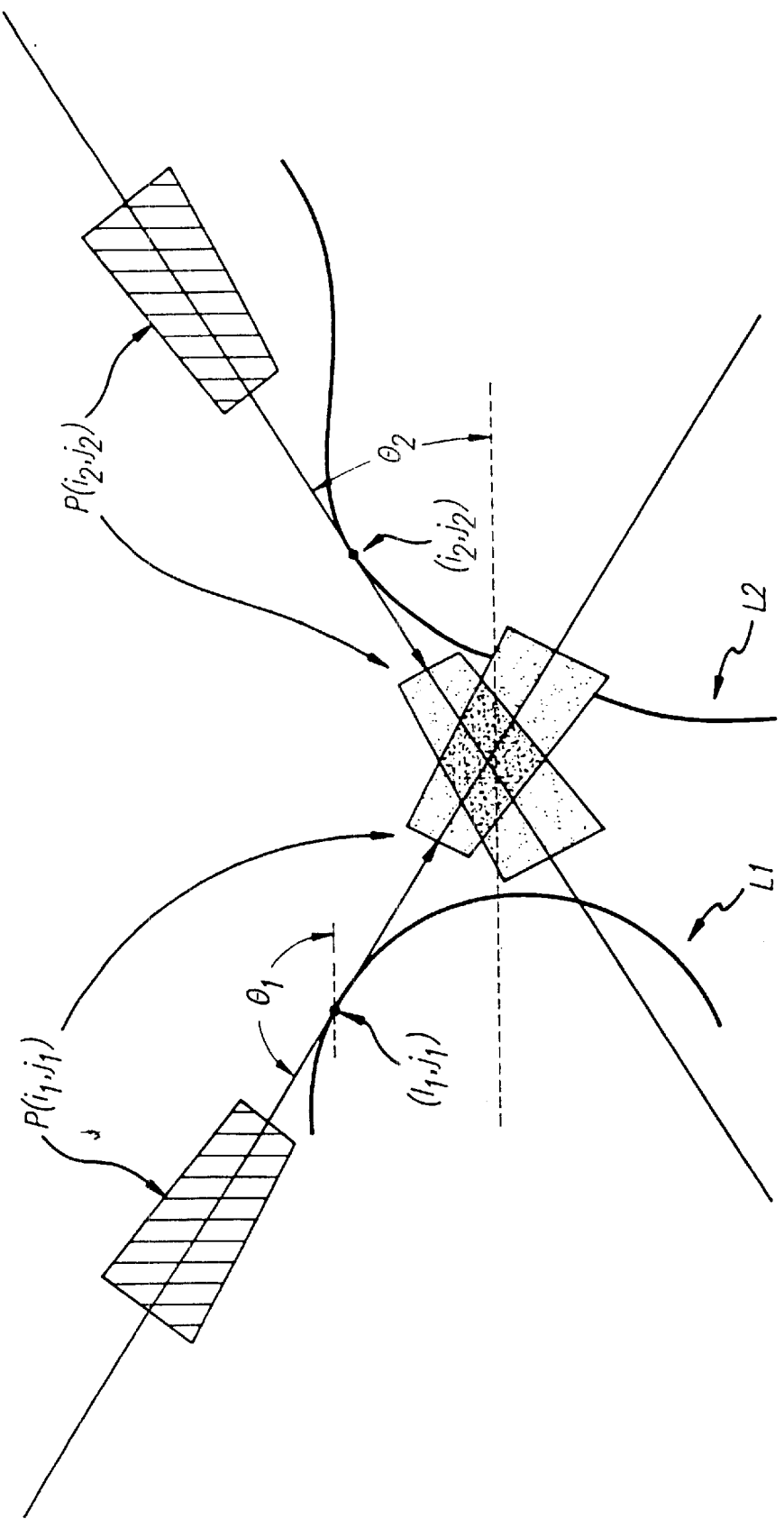
FIG. 7 is a conceptual diagram showing the determination of potential regions of intersection for two points in a line image in accordance with the present invention, the two lines not being associated with a common spiculation.
Figure 8:
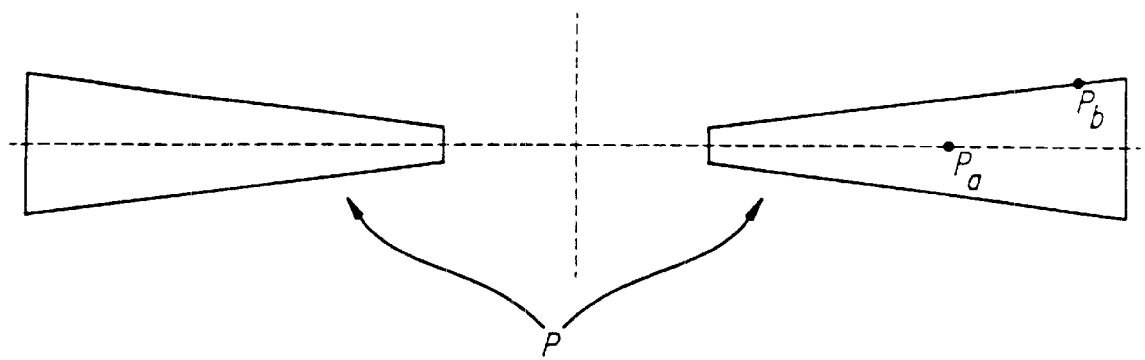
FIG. 8 shows a typical predetermined pattern P used to generate regions of potential intersection in the spiculation detection algorithm according to the present invention.

FIG. 7 shows a conceptual diagram of the addition of patterns for each pixel in the line image. Shown in FIG. 7 are two points (i1,j1) and (i2,j2) which lie somewhere along lines L1 and L2, respectively. Regions of potential overlap for these two points, denoted P(i1,j1) and P(i2,j2), are shown superimposed over the line image for clarity. The regions of potential overlap P(i1,j1) and P(i2,j2) are simply rotated versions of a predetermined pattern P, shown in FIG. 8, which have been translated to be centered on the points (i1,j1) and (i2,j2), respectively, the amount of rotation being a direction image value THETA(i1,j1) for pixel (i1,j1) and THETA(i2,j2) for pixel (i2,j2). As shown in FIG. 8, the predetermined pattern P is of a split rectangular or trapezoidal shape having a high aspect ratio (i.e., a large width to height ratio).

Figure 9:
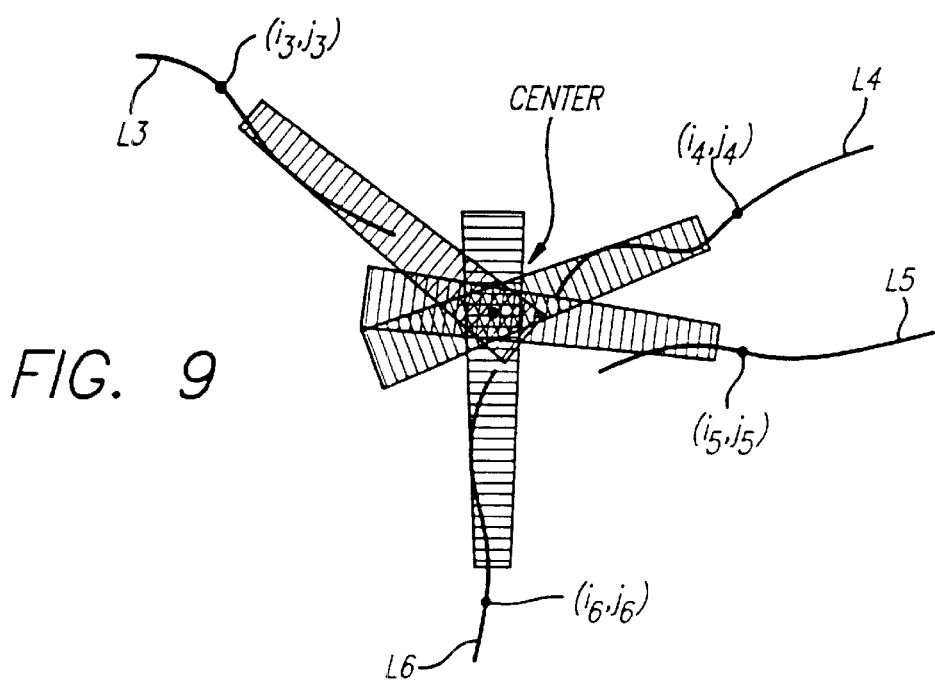
FIG. 9 is a conceptual diagram showing the determination of potential regions of intersection for two points in a line image in accordance with the present invention, the two lines being associated with a common spiculation.

As can be seen in FIG. 7, because of the choice of a high-aspect-ratio pattern P, the region of potential overlap P(i1,j1) for the point (i1,j1) is roughly equivalent to a tangent of the line L1 containing the point (i1,j1), the tangent having been truncated at a distance corresponding to the length of the pattern P. The spiculation detection algorithm according to the present invention is based on the principle that any two lines L1 and L2 belonging to the same spiculation will have an entire series of points (i1,j1) and (i2,j2) whose tangents will overlap near a common point at the center of the spiculation. In FIG. 6, the lines denoted L1 and L2 do not belong to a spiculation, and it can be seen that the regions of pattern overlap for various points (i1,j1) and (i2,j2) along lines L1 and L2 will be dispersed throughout many locations in the cumulative array C. In contrast, as shown in FIG. 9, lines L3, L4, L5, and L6, having pixels including exemplary pixels (i3,j3), (i4,j4), (i5,j5), and (i6,j6), respectively, belonging to the same spiculation will have repeated overlap of tangents near the center of the spiculation.

Accordingly, if the regions of potential overlap, denoted generally as P(x,y), are accumulated into the cumulative array C, the cumulative array C will contain higher values at locations corresponding to spiculations. The greater the number of intersecting, radiating lines at a spiculation, the greater the value of the cumulative array C at the center of that spiculation.

Importantly, it is noted that the spiculation detection algorithm according to the present invention is a "forward direction" algorithm. Each pixel in the line image is processed only once in generating the cumulative array. Furthermore, a lookup table procedure is used which directly maps the digital mammogram pixels (i,j) lying along lines and having direction values THETA(i,j) into regions of covered pixels in the cumulative array C, based on the shape of the predetermined pattern P. This provides for an especially fast production of the cumulative array C.

According to another embodiment of the invention, the lookup table procedure for mapping points and directions into regions of potential intersection incorporates weighting values in the predetermined pattern P. Thus, instead of simply adding a "1" to the cumulative array C for every array location falling inside the pattern P(i1,j1), a weighting value may be used. For example, points corresponding to a point Pa in the predetermined pattern P of FIG. 8, lying directly along the center line of P, may be assigned a heavier weight than a point Pb lying along the periphery of the predetermined pattern P. This is because peripheral points are less likely than center line points to lie directly at the center of the spiculation.

The predetermined pattern P is designed in an empirical manner to maintain accuracy (minimizing false positives) while maximizing precision in finding spiculations of the appropriate size. In a prime example, it may be desirable to detect spiculations which have a radius of around 5 mm, because if the spiculations grow to a size much larger a 5 mm radius, it may be too late to stop the spread of the cancer. For a digital mammogram image in which 1 pixel corresponds to 200 microns, or in which 25 pixels equals 5 mm, it has been found that a predetermined pattern P having its opposing trapezoids extending from about 15 pixels to about 80 pixels from the center, with a width ranging from about 4 pixels near the center to 20 pixels at the periphery, yields satisfactory results. It is noted, however, that the scope of the invention may encompass a wide variety of shapes and dimensions of the predetermined pattern P, as empirically and/or analytically determined to optimize system performance based on desired performance parameters.

Figure 10:
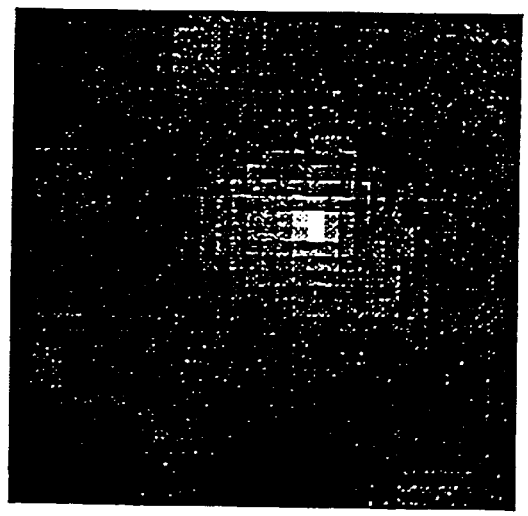
FIG. 10 shows an image representing a portion of the cumulative array resulting from the performance of a spiculation algorithm on a digital mammogram image in accordance with the present invention.

FIG. 10 shows in a pictorial fashion the cumulative array C generated from the line image of FIG. 5. A side-by-side comparison of FIG. 10 and FIG. 5 shows that the cumulative array C contains a local maximum at a point corresponding to the intersection of several lines forming a spiculation in the line image of FIG. 5. Using one of many methods, the cumulative array C may be used to generate highlighted regions for display on the display device 118 of FIG. 1. For example, the cumulative array C may be thresholded at a certain level, and points exceeding the threshold value may be displayed. Alternatively, a selected number of top values in the cumulative array C may be selected for display. Other methods may be used as well as will be discussed below.

Figure 11:
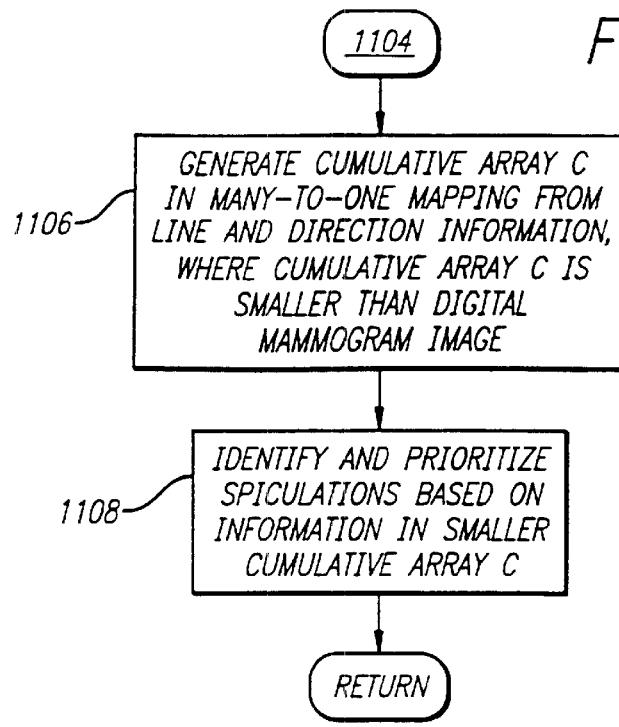
FIG. 11 is a flowchart representing a spiculation detection algorithm in accordance with a further embodiment of the present invention.

FIG. 11 shows a flowchart showing a spiculation detection and prioritization step 1104 representing a preferred embodiment of the invention. The spiculation detection and prioritization step 1104 is to be performed in place of the spiculation detection and prioritization step 304 of FIG. 3. In the preferred embodiment, the M×N line and direction images have been computed according to the above described methods. However, in the preferred embodiment of step 1104, the cumulative array C is smaller than the M×N digital mammogram image, having dimensions AM×BN, where A<1 and B<1. For example, A and B may both be chosen as 0.25, in which case the cumulative array C has dimensions 0.25M×0.25N. Step 1104 comprises the step 1106 of generating the cumulative array C in a many-to-one mapping, followed by the step 1108 of identifying and prioritizing spiculations based on information in the cumulative array C.

In step 1106, a region of potential intersection is determined for each pixel (i,j) in the digital mammogram image based on the line information and direction information for the pixel (i,j). For each digital mammogram image pixel (i,j) having line image information with a value "1", the cumulative array C is incremented by a constant value for each pixel located in a region corresponding to a predetermined pattern P' centered at a pixel location (k,l) in the cumulative array C. In particular, the predetermined pattern P' is a proportionally reduced version of the function P shown in FIG. 8 for application to the smaller cumulative array C, and (k,l) is chosen such that k=INT(Ai) and l=INT(Bj). Thus, for example, where P extended from an inner radius of 15 pixels to 80 pixels, the array P' would extend from about 4 pixels to 20 pixels for A=B=0.25. As before, the region of potential intersection is the predetermined pattern P' rotated by the amount THETA(i,j) corresponding to the digital mammogram image pixel (i,j).

The step 1106 is preferable to step 602 in that fewer computations are needed to produce the cumulative array C, thus saving time. This is because fewer pixels in the cumulative array C are incremented for a given pixel (i,j) in the digital mammogram image. The computation time is reduced by a factor roughly equal to the product AB, because only that proportion of pixels in the cumulative array C are incremented when compared to the algorithm of step 602.

Figure 12:
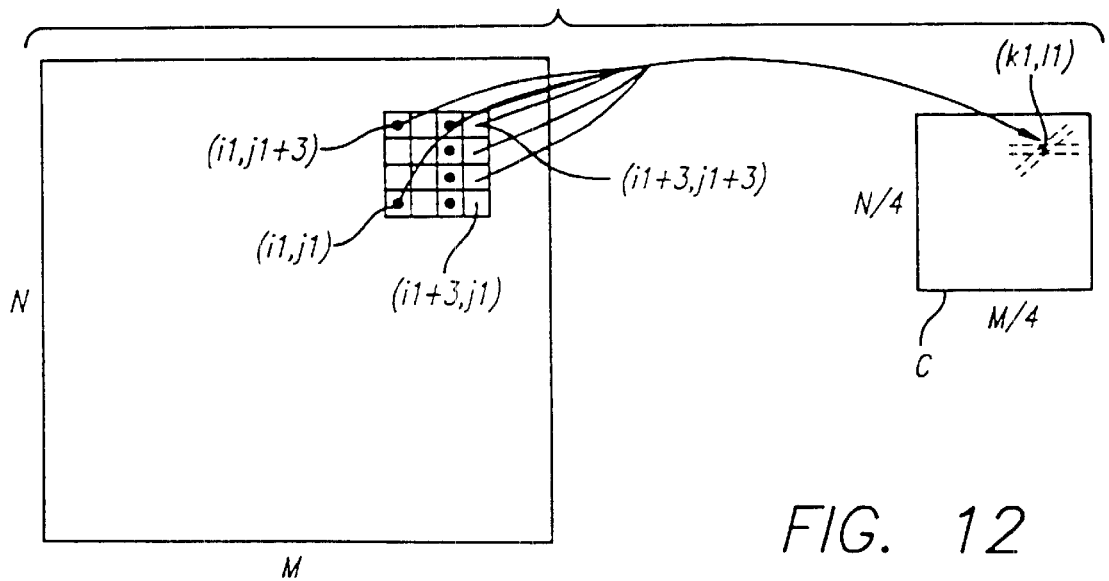
FIG. 12 is a conceptual diagrams showing pixel mappings related to the steps of FIG. 11.

FIG. 12 diagrammatically illustrates the "many-to-one" mapping which occurs between the M×N digital mammogram image and the AM×BN cumulative array, for the case where A=B=0.25. The mapping is "many-to-one" because the same pixel (k1,l1) in the cumulative array acts as the center for the accumulation of up to 16 different regions of potential intersection corresponding to points (i1,j1) . . . (i1+3,j1+3) in the digital mammogram image.

Measurements have indicated that the CAD system 100 performing spiculation detection in accordance with the present invention represents a drastic increase in speed over the Karssemeijer algorithm. Indeed, it has been found that spiculation detection using the step 304 of FIG. 6 results in a several-fold increase in the speed of spiculation detection. In particular, it has been found that where the Karssemeijer method takes 1–2 hours to generate an output, the spiculation detection method using the step 304 of FIG. 6 takes less than 20 minutes. Even further, it has been found that if the CAD system 100 uses the step 1104 of FIG. 11 in spiculation detection, the computation time is reduced to about 20 seconds. This drastic increase in speed allows the CAD system 100 to be used in everyday radiology practice to increase the accuracy and reliability of the spiculation detection process while not slowing down the radiologist.

Other embodiments for improving results are described below. It will be noted that while the following disclosed principles apply to either the case where the cumulative array C is a full-scale M×N array or a smaller AM×BN array, the case where C is a full-scale array is described for conciseness and clarity of disclosure.

Figure 13C:
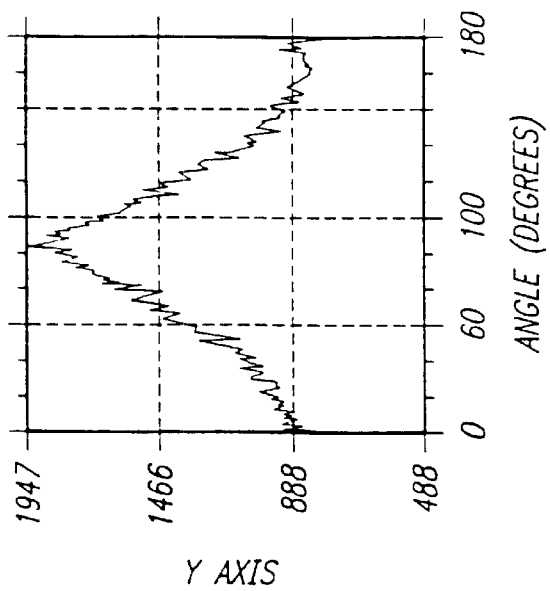
FIGS. 13(c) and 13(d) show a histogram of angle information in a digital mammogram and a corresponding weighting function WT(theta) computed from the histogram.
Figure 13D:
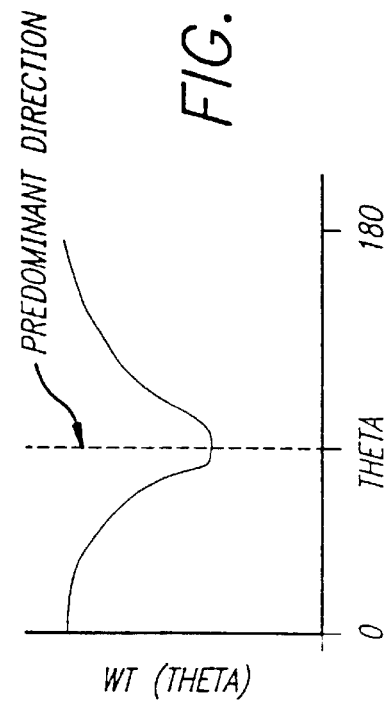
Figure 13A:
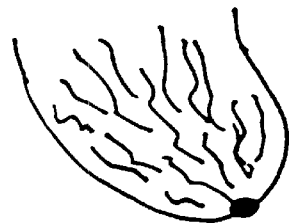
FIG. 13(a) is a simplified diagram of a typical line image corresponding to a digital mammogram image.
Figure 13:
FIGS. 13(b1) and 13(b2) are representative diagrams of eccentric and circular spiculations, respectively.
Figure 13:

FIG. 13 illustrates a method of computing weights WT(theta) for weighting regions of potential intersection before accumulation into the cumulative array C in accordance with another embodiment of the present invention. It has been found that lines in a digital mammogram of a real breast will tend to be directed toward the nipple of the breast, as shown in FIG. 13(a). The presence of many near-parallel lines tends to cause detection of highly eccentric spiculations as shown in FIG. 13(b1), resulting in false positives in the spiculation detection algorithm. It is more desirable to locate and identify the circular, quasi-symmetric-type spiculations as shown in FIG. 13(b2), which correspond to spiculations which are more likely to be suspicious, than to identify the highly eccentric spiculations of FIG. 13(b1), which are often simply the result of lines facing near the predominant direction which incidentally intersect.

It has been found that weighting the regions of potential intersection by an appropriate function WT(THETA(i,j)) for the pixel being accumulated will appropriately de-emphasize predominant-direction lines and emphasize lines near the perpendicular to the predominant direction.

The function WT(theta) is computed by first computing statistical information, such as a histogram H(theta), of pixel directions THETA(i,j) following step 302 of FIG. 3. A typical distribution H(theta) is shown in FIG. 13(c), the predominant direction indicated being near theta=90 degrees in the example shown. The function WT(theta) is then determined by plotting an inverse to H(theta) as shown in FIG. 13(d). Generally, WT(theta) will be a minimum where H(theta) is a maximum.

The exact shape of the plot of WT(theta) may be varied according to empirical data for yielding the best results. However, WT(theta) will have a general shape as shown in FIG. 13(d). The cumulative array C is incremented at those locations falling within the rotated and shifted region P(i,j), and is incremented by an amount equal to WT(THETA(i,j)) for the pixel (i,j) instead of a constant value, as described in previous embodiments. In this manner, pixels located along lines in the predominant direction are de-emphasized in generating the cumulative array C. Also, pixels located along lines near-perpendicular to the predominant direction are emphasized. This results in the ability to detect spiculations with greater accuracy and precision, and with fewer false positives due to incidental, highly eccentric spiculations.

Figure 14:
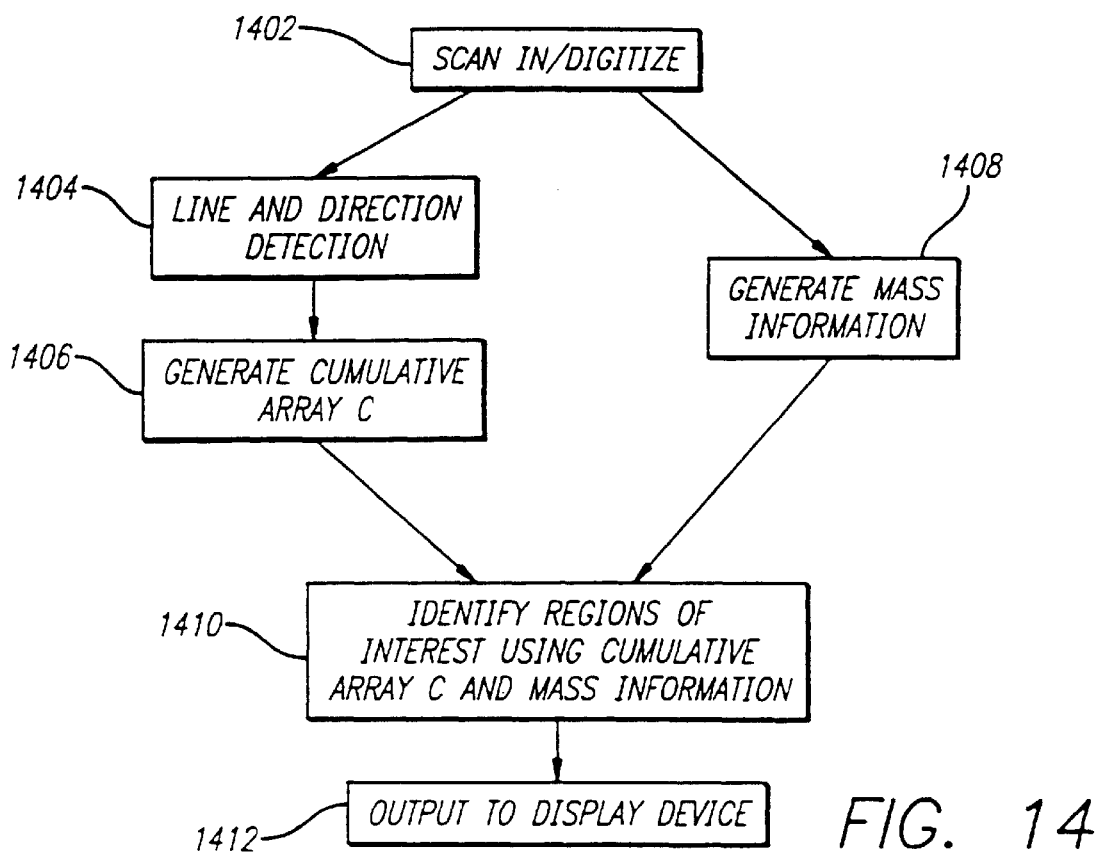
FIG. 14 shows a flowchart representing spiculation and mass detection algorithms in accordance with a further embodiment of the present invention.

FIG. 14 shows a flowchart illustrating steps for identifying regions of interest to the radiologist in an x-ray mammogram according to another embodiment of the present invention. FIG. 14 shows a step 1402 similar to step 202 disclosed above, a step 1404 similar to step 302 disclosed above, and a step 1406 similar to step 602 disclosed above. Performed in parallel with steps 1404 and 1406, however, is a step 1408 for generating mass information. Step 1408 may be performed by using steps known in the art for detecting, classifying, and prioritizing masses. Such steps are disclosed, for example, in Yin et al., "Computerized Detection of Masses in Digital Mammograms: Analysis of Bilateral Subtraction Images," Med. Phys. 18(5) (September/October 1991), and in U.S. Pat. No. 5,133,020 to Giger et al, entitled "Automated Method and System for the Detection and Classification of Abnormal Lesions and Parenchymal Distortions in Digital Medical Images," the disclosures of which are hereby incorporated by reference into the present application. Mass information may include, but is not limited to, mass events, each event comprising, for example, mass centroid location, mass area, mass elongation, and mass contrast. Mass information may also include information derived from region-growing algorithms known in the art and described, for example, in Gonzalez, *Digital Image Processing* at pp. 369–375, the disclosure of which is incorporated herein by reference.

FIG. 14 also shows a step 1410 for identifying regions of interest using the cumulative array C along with the above mass information for detecting regions of interest in the digital mammogram. It has been found that mass information may be used in conjunction with spiculation information for reducing certain forms of false positives resulting from radial lines that originate from accidental crossing of lines, or from objects such as "radial scars" from previous biopsies. Many of these false positives can be eliminated at step 1410 by requiring, for local maxima in the cumulative array C, or for other spiculation locations resulting from operations such as thresholding of the cumulative array C, the existence of a central mass density from which the lines originate. Thus, as an example of this embodiment, if there is no mass associated with a local maximum in the array C, as dictated by the above mass information, then this point will not be identified to the radiologist as a highlighted region even though the spiculation identification criteria would otherwise have been met. In this way, false positives are reduced.

FIG. 15 shows a novel alternative for step 1408 in determining mass information according to another embodiment of the present invention. It has been found that the spiculation detection algorithm as exemplified by steps 302 and 304 may be modified for detecting masses and for computing mass information for use in step 1410. In particular, it has been found that if at step 302, the gradient of the digital mammogram image is computed instead of the line and direction images, and then the step 304 is executed using the gradient intensity and gradient direction for each pixel (i,j), instead of the binary line value and line direction THETA(i,j) for each pixel (i,j), respectively, the resulting cumulative array, which will now be called a "sphericity array," will contain high values at mass locations instead of spiculation locations.

Shown at FIG. 15 is a step 1502 for computing the gradient of the digital mammogram image using methods known in the art, such as the Sobel matrix method. Resulting from the step 1502 is a gradient plane which, for each pixel (i,j), comprises a gradient intensity value and a gradient direction value. Shown at step 1504 is a step for determining, for each gradient plane pixel (i,j), a "region of potential centroid" using the gradient intensity value and the gradient direction value for the pixel (i,j). The region of potential centroid is computed in manner similar to the region of potential intersection described above, using gradient intensity instead of the binary line information and using gradient direction instead of line direction THETA(x, y). Shown at step 1506 is the step of accumulating, in a manner similar to that for regions of potential intersection for the previous spiculation detection embodiments, the regions of potential centroids into the sphericity array. Finally, shown at step 1508 is the step of using the information in the sphericity array for determining mass information, using steps similar to those for using the cumulative array information to detect spiculations. The mass information may then be used in conjunction with the spiculation information at step 1410 of FIG. 14, as discussed previously. Using this approach, the mass information may be computed faster than in prior art mass information computation algorithms by using a forward direction algorithm.

Another embodiment of the present invention may be used at step 1410 for handling intermediate cases of spiculations. There is a class of breast masses that are not heavily spiculated, but rather circumscribed with small spiculations or very few spiculations which, while producing some signal in the cumulative array C, would not otherwise be detected as spiculations by the spiculation detection algorithm disclosed. A technique known as a "local attention" algorithm may be used for these intermediate cases as follows. Strong (high probability) circumscribed mass candidates are detected by algorithms such as those disclosed for step 1408 discussed previously. Once regions containing strong circumscribed mass candidates are identified, the thresholds such as those described above for detecting high probability spiculation candidates are lowered in these regions. When this technique of "local attention" is employed in this manner, the spiculations identified by means of the reduced thresholds are used to further classify and describe a measure of "spiculatedness" for a circumscribed mass in order to increase its level of concern.

Thus, in this embodiment of the invention, local attention is given to the cumulative array near locations having a strong circumscribed mass candidate. The cumulative array is thresholded by a first threshold value in a first region not including the strong circumscribed mass candidate location, whereas the cumulative array is thresholded by a second value less than the first value in a second region which includes said strong circumscribed mass candidate. In this manner, spiculations which otherwise would have fallen below a threshold value in the cumulative array are detected when associated with a strong circumscribed mass candidate, for assigning a value of spiculatedness to the circumscribed mass candidate.

FIG. 16 shows a method for locating noneccentric spiculations for increased precision, accuracy, and reduction of false positives according to a preferred embodiment of the invention. In general, this preferred embodiment is directed toward weighting the regions of potential intersection P(i,j) for each image pixel and accumulating the weighted regions into separate accumulation arrays having different characteristics. The separate accumulation arrays are then combined in a novel manner to produce a spiculation output array for locating noneccentric spiculations. It is to be noted that the method of FIG. 16 as described below may be modified for operating in conjunction with the statistics-based emphasis method of FIG. 13, the smaller cumulative array method of FIGS. 11 and 12, and/or the parallel mass-detection and processing method of FIG. 14.

FIG. 16 shows a scanning and digitizing step 1602 similar to step 202, and a line and direction detection step 1604 which operates in a manner similar to step 302. FIG. 16 further shows a step 1606 for generating a first accumulation plane ACC1, a second accumulation plane ACC2, and a third accumulation plane ACC3. The accumulation planes: ACC1, ACC2, and ACC3 are each computed in a manner similar to the computation of the cumulative array C described with respect to previous embodiments, except that the amount by which the accumulation planes are incremented is equal to functions W1(i,j), W2(i,j), and W3(i,j), respectively, for those locations in the accumulation planes falling within the translated and rotated predetermined pattern P(i,j).

Keeping in mind that the values THETA(i,j) were computed at step 1604, the values for W1, W2, and W3 are as follows:

$$W1(i,j)=\cos^2(THETA(i,j)) \tag{4}$$

$$W2(i,j)=\sin^2(THETA(i,j)) \tag{5}$$

$$W3(i,j)=2\cos(THETA(i,j))\sin(THETA(i,j)) \tag{6}$$

FIG. 16 also shows a step 1608 for generating a spiculation activity plane ACT(i,j) and a spiculation eccentricity plane ECC(i,j), which are to be computed according to the following equations:

$$ACT(i,j)=W1(i,j)+W2(i,j) \tag{7}$$

$$ECC(i,j)=\sqrt{(W1(i,j)-W2(i,j))^2+W3^2(i,j)} \tag{8}$$

Generally, when computed according to the above equations, the spiculation activity plane ACT(i,j) will be higher in those areas corresponding to spiculations, and both ACT(i,j) and the spiculation eccentricity plane ECC(i,j) will be low in those areas not corresponding to spiculations. Further, it has been found that, generally speaking, the spiculation eccentricity plane ECC(i,j) will be higher in those areas corresponding to more eccentric spiculations exemplified by FIG. 13(b1), but will be lower in those areas corresponding to more circularized spiculations exemplified by FIG. 13(b2). In view of these characteristics, it has been found that a spiculation output array SO(i,j) may be computed from ACT(i,j) and ECC(i,j) such that SO(i,j) has desired characteristics in that SO(i,j) is high in those areas having circularized (i.e., noneccentric) spiculations and low otherwise. The step of computing So(i,j) is shown at step 1610 of FIG. 16.

In particular, it has been found that SO(i,j) may obtain the desired characteristics when computed according to the following equation:

$$SO(i,j)=R1*ACT(i,j)-R2*ECC(i,j) \qquad (9)$$

In the above equation, R1 and R2 are constants greater than zero. It has further been found that better results are obtained for R1>R2, and in a preferred implementation, R1=2 while R2=1.

FIG. 16 further shows a step 1612 for generating mass information related to the digital mammogram image. It is to be appreciated that the step 1612 may be performed serially or in parallel with the steps 1604–1610. FIG. 16 further shows a step 1614 for identifying regions of interest and a step 1616 for displaying the regions of interest.

In general, the step 1614 of FIG. 16 may be performed in a manner similar to the step 1410 of FIG. 14. However, it is to be appreciated that, in light of the above descriptions, there have been described several features which, according to another embodiment of the present invention, may be taken together in one of many ways for indicating regions of interest responsive to the presence of spiculated or stellate masses. Table 1 includes a non-limiting list of some of these features.

TABLE 1

| Feature | Name | Description |
| --- | --- | --- |
| 1. ECC (i, j) | Eccentricity plane | Inversely related to circularity of spiculations centered at (i, j) |
| 2. ACT (i, j) | Spiculation activity plane | Related to the presence of spiculations centered at (i, j) |
| 3. SO (i, j) | Spiculation output plane | Example: SO (i, j) = 2*ACT (i, j) − ECC (i, j) |
| 4. Sphericity (i, j) | Sphericity plane | Related to presence of circumscribed masses centered at (i, j) |
| 5. C (i, j) | Cumulative array | Related to the presence of spiculations centered at (i, j) |
| 6. Mass events | | Examples include mass centroid location, mass area, mass elongation, and mass contrast. |

A method of linear classifiers using rule-based cuts (thresholds) on each feature, or in combination of two features taken together, may be used to determine regions of interest. By way of non-limiting example, simply the value of SO(i,j) may be thresholded by a threshold value. In another example, a plot may be made of (1/ECC(i,j)) versus elongation for events having a value of mass area above a certain threshold. Minimum threshold values along the abscissa and ordinate may be selected, and events falling in the upper right quadrant may be selected as regions of interest, with a view toward not identifying large elongated masses, as determined by mass algorithms, unless they are associated with a highly circular spiculation, as determined by spiculation algorithms. The values of thresholds used may be determined empirically by examining the distribution or true and false positive indications.

By way of further non-limiting example, a plot of SO(i,j) versus (1/ECC(i,j)) may be made, and events falling within an upper right quadrant of the plot may be selected, with a view toward identifying large magnitude spiculations which are also highly circular. It can be seen that many linear classifier methods may be used based on the entries of Table 1 falling within the scope of the present invention. It is also noted that a standard back-propagation neural network classifier may be used in conjunction with the features of Table 1 and other features, the neural network classifier being trained on multiple examples of true and false positive indications.

While preferred embodiments of the invention have been described, these descriptions are merely illustrative and are not intended to limit the present invention. For example, although the embodiments of the invention described above were in the context of a system for computer aided diagnosis and detection of breast carcinoma in x-ray films, those skilled in the art will recognize that the disclosed methods and structures are readily adaptable for broader applications. For example, the invention is applicable to many other types of CAD systems for detection of other types of medical abnormalities.

What is claimed is:

1. A method of determining regions of interest in an image that is an array of pixels comprising the steps of:
    at each pixel in the image, determining if the pixel is a portion of a line and determining the direction of the line, if any;
    generating a cumulative array of cells that identifies regions of interest in the image by:
        at each pixel in the image that is a portion of a line, using the line direction information to define a region in the cumulative array along said line, and
        at each cell in the cumulative array within the region defined with the line direction information, incrementing a numerical value associated with the cell; and
    identifying regions of interest in the image by identifying those cells in the cumulative array that have numerical values that are local extrema.

2. The method of claim 1, wherein the region of interest is identified by a local maximum in the cumulative array.

3. The method of claim 1 further comprising the step of thresholding the cumulative array to identify regions of interest near locations where said cumulative array exceeds a threshold value.

4. The method of claim 1 comprising the steps of:
    computing a gradient surface from said image, each pixel in the gradient surface having a gradient intensity value and a gradient direction value; and
    determining a region of interest using the gradient intensity value and gradient direction value of the pixels.

5. The method of claim 4 wherein the line direction information is the gradient direction value.

6. The method of claim 5 wherein the region in the cumulative array is spaced from a projection of the pixel onto the cumulative array and is aligned with the gradient direction value.

7. The method of claim 6 the region extends from a first radial distance to a second radial distance from the projection of the pixel onto the cumulative array.

8. The method of claim 4 wherein, for each region defined in the cumulative array, each cell in the cumulative array within that region is incremented by a numerical value corresponding to the gradient intensity value for the pixel associated with that region.

9. A method of determining regions of interest in an image that is an array of image elements comprising the steps of:
- at each image element in the image, determining if the image element is a portion of a line and determining the direction of the line, if any;
- generating a cumulative array of cells that identifies regions of interest in the image by:
  - at each image element in the image that is a portion of a line, using the line direction to define a region in the cumulative array along said line, and
  - at each cell in the cumulative array within the region defined with the line direction, incrementing a numerical value associated with the cell; and
  - identifying regions of interest in the image by identifying those cells in the cumulative array that have numerical values that are local extrema.

10. The method of claim 9 wherein the region of interest is identified by a local maximum in the cumulative array.

11. The method of claim 9 further comprising the step of thresholding the cumulative array to identify regions of interest near locations where said cumulative array exceeds a threshold value.

12. The method of claim 9 comprising the steps of:
- computing a gradient surface from said image, each image element in the gradient surface having a gradient intensity value and a gradient direction value; and
- determining a region of interest using the gradient intensity value and gradient direction value of the image elements.

13. The method of claim 12 the line direction is specified by the gradient direction value.

14. The method of claim 13, wherein the region in the cumulative array is spaced from a projection of the pixel onto the cumulative array and is aligned with the gradient direction value.

15. The method of claim 14, wherein the region extends from a first radial distance to a second radial distance from the projection of the image element onto the cumulative array.

16. The method of claim 12, wherein, for each region defined in the cumulative array, each cell in the cumulative array within that region is incremented by a numerical value corresponding to the gradient intensity value for the image element associated with that region.

17. A method of determining regions of interest in an image that is an array of image elements comprising the steps of:
- at each image element in the image, determining if the image element contains a directional feature and determining directional information representative of the directional feature, if any;
- generating a cumulative array of cells that identifies regions of interest in the image by:
  - at each image element in the image that contains a directional feature, using the directional information to define a region in the cumulative array, and
  - at each cell in the cumulative array within the region defined with the directional information, incrementing a numerical value associated with the cell; and
- identifying regions of interest in the image by identifying those cells in the cumulative array that have numerical values that are local extrema.

18. The method of claim 17 wherein the region of interest is identified by a local maximum in the cumulative array.

19. The method of claim 17 comprising the step of thresholding the cumulative array to identify regions of interest near locations where said cumulative array exceeds a threshold value.

20. The method of claim 17 comprising the steps of:
- computing a gradient surface from said image, each image element in the gradient surface having a gradient intensity value and a gradient direction value; and
- determining a region of interest using the gradient intensity value and gradient direction value of the image elements.

21. The method of claim 20 wherein the directional information is specified by the gradient direction value.

22. The method of claim 21 wherein the region in the cumulative array is spaced from a projection of the pixel onto the cumulative array and is aligned with the gradient direction value.

23. The method of claim 22 wherein, the region extends from a first radial distance to a second radial distance from the projection of the image element onto the cumulative array.

24. The method of claim 20 wherein, for each region defined in the cumulative array, each cell in the cumulative array within that region is incremented by a numerical value corresponding to the gradient intensity value for the image element associated with that region.

* * * * *